(12) United States Patent
Eveland et al.

(10) Patent No.: US 10,786,141 B2
(45) Date of Patent: Sep. 29, 2020

(54) CAP ASSEMBLY FOR ENDOSCOPE

(71) Applicant: AMERICAN STERILIZER COMPANY, Mentor, OH (US)

(72) Inventors: Randal W. Eveland, Kirtland, OH (US); Nancy A. Robinson, Mentor, OH (US); Sarah Lynn Lazzara, Mentor, OH (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 410 days.

(21) Appl. No.: 15/868,250

(22) Filed: Jan. 11, 2018

(65) Prior Publication Data

US 2018/0279859 A1 Oct. 4, 2018

Related U.S. Application Data

(60) Provisional application No. 62/479,395, filed on Mar. 31, 2017.

(51) Int. Cl.
*A61B 1/00* (2006.01)
*A61L 2/26* (2006.01)
*A61L 2/20* (2006.01)

(52) U.S. Cl.
CPC .......... *A61B 1/00137* (2013.01); *A61L 2/208* (2013.01); *A61L 2/26* (2013.01); *A61L 2202/13* (2013.01); *A61L 2202/24* (2013.01)

(58) Field of Classification Search
None
See application file for complete search history.

(56) References Cited

U.S. PATENT DOCUMENTS

| | | |
|---|---|---|
| 5,634,880 A | 6/1997 | Feldman et al. |
| 5,868,667 A | 2/1999 | Lin et al. |
| 2009/0028753 A1 | 1/2009 | Bala |
| 2009/0081767 A1 | 3/2009 | Ogawa et al. |
| 2010/0064456 A1* | 3/2010 | Ferlic ............... A61M 39/20 15/104.94 |
| 2011/0064606 A1 | 3/2011 | Foltz et al. |
| 2014/0100425 A1 | 4/2014 | Metras |

FOREIGN PATENT DOCUMENTS

JP 2004-016543 1/2004

OTHER PUBLICATIONS

International Search Report issued in corresponding International Patent Application No. PCT/US2018/023498, dated May 31, 2018.

* cited by examiner

*Primary Examiner* — Timothy J Neal
(74) *Attorney, Agent, or Firm* — Kusner & Jaffe

(57) ABSTRACT

A cap assembly for attachment to an equalization port on an endoscope, comprising a tubular housing defining an internal chamber, a mounting section releasably attached to the housing in fluid-tight fashion and attachable to the equalization port of an endoscope, wherein the internal chamber communicates with the equalization port; a barrier layer formed of a reactive material disposed within the internal chamber, a first cavity defined between the barrier layer and a first end of the housing; a second cavity defined between the barrier layer and the mounting section, the second cavity dimensioned to receive an indicator test strip that is capable of detecting a gaseous germicide; and a filter layer disposed between the barrier layer and the first end of the housing.

17 Claims, 4 Drawing Sheets

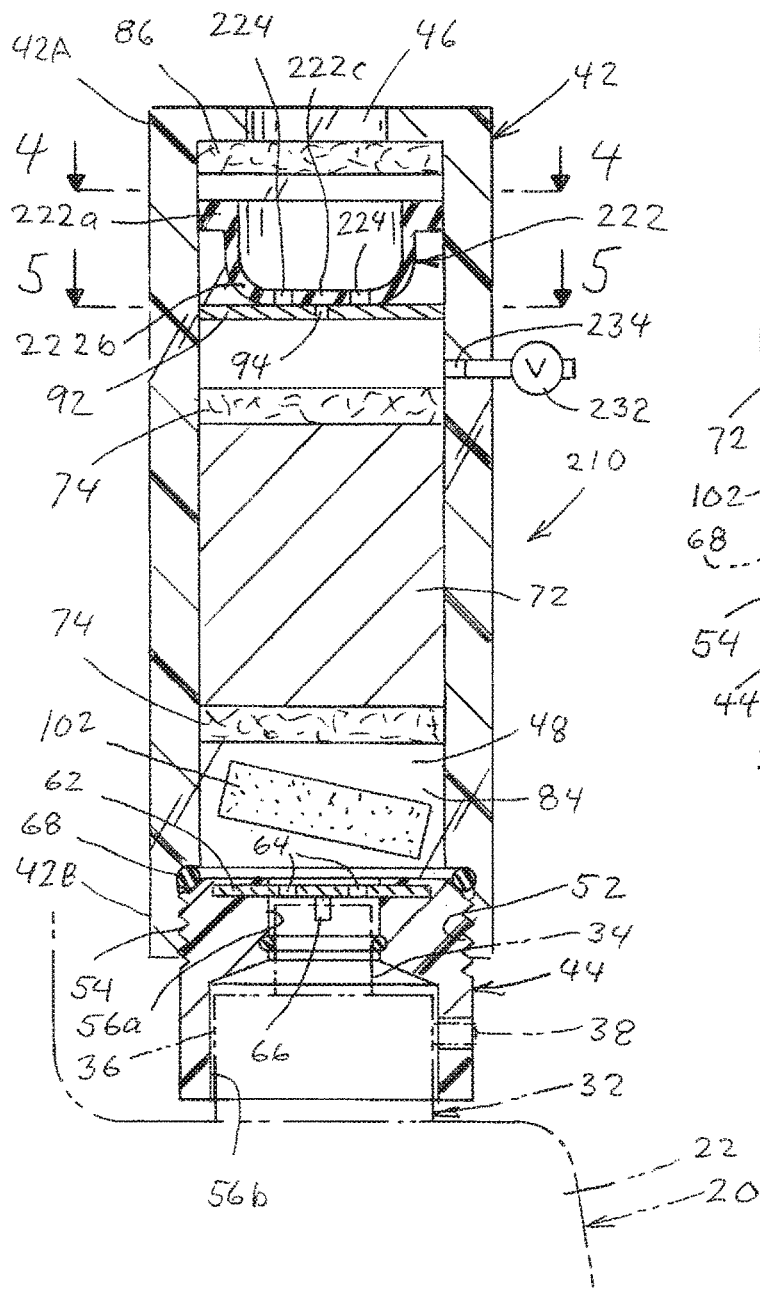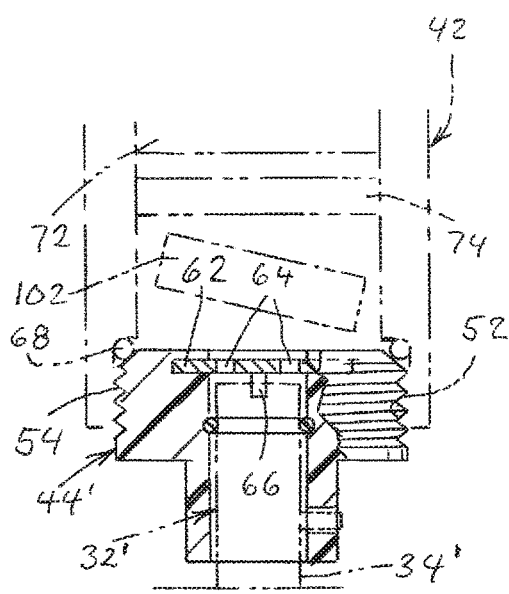
FIG. 3
FIG. 6

CAP ASSEMBLY FOR ENDOSCOPE

FIELD OF THE INVENTION

The present invention relates generally to medical endoscopes and more particularly to a device for protecting the internal structures of an endoscope during a decontamination (sterilization or high level disinfection) process.

BACKGROUND OF THE INVENTION

Endoscopes, and in particular flexible endoscopes, are widely used in the medical industry. Maintaining precise movement of components within an endoscope, especially within the tip end of the endoscope and the insertion tube of the endoscope, is critical to the proper operation and function thereof. Original equipment manufacturers (OEM) often use a solid lubricant within endoscopes to ensure proper lubrication and function of internal parts of the endoscope. A ground PTFE powder is often used for small diameter surgical endoscopes. For larger endoscopes, such as a gastrointestinal (GI) endoscope, a molybdenum disulfide ($MoS_2$) compound is used. It is well known that surgical endoscopes must be "processed," i.e., decontaminated, between uses in medical procedures. Flexible surgical endoscopes are currently processed in low pressure hydrogen peroxide gas sterilizers. Gastrointestinal (GI) endoscopes are not currently decontaminated with hydrogen peroxide gas. Typically, an ethylene oxide (EO) or a liquid chemical decontamination process is used. For low pressure gaseous decontamination processes, such as EO, it is known to open the internal components of the device to the decontamination process, i.e., to the EO gas, such that the EO gas freely enters the internal scope compartment.

While use of vaporized hydrogen peroxide in low pressure sterilization processes finds advantageous applications in decontaminating endoscopes, it has been found that molybdenum disulfide can react with hydrogen peroxide, yielding molybdenum oxide ($MoO_3$) and sulfuric acid ($H_2SO_4$). It is also believed that hydrogen sulfide ($H_2S$) is generated. As will be appreciated, sulfuric acid can negatively impact the internal components of the endoscope, and its acidic nature can also cause material issues to the internal components and the external covering of the endoscopes. It is also found that other gaseous oxidizing decontamination chemistries can have deterious effects on the internal components of an endoscope. The present invention provides a protective cap assembly for attachment to an endoscope to prevent oxidizing chemistries and, in particular, hydrogen peroxide from entering the interior portions of an endoscope during a low pressure decontamination cycle.

SUMMARY OF THE INVENTION

A cap assembly for attachment to an equalization port on an endoscope, comprising a tubular housing having a first end and a second end and defining an internal chamber extending from the first end to the second end. A mounting section is releasably attached to the second end of the housing in fluid-tight fashion. The mounting section is dimensioned to be attached to the equalization port of an endoscope in fluid-tight fashion, wherein the internal chamber communicates with the equalization port. A barrier layer, formed of a reactive material that is capable of absorbing or breaking down a gaseous germicide (sterilant or high level disinfectant), is disposed within the internal chamber between the first end and the second end of the housing. A first cavity is defined between the barrier layer and the first end of the housing. A second cavity is defined between the barrier layer and the mounting section, the second cavity being dimensioned to receive an indicator test strip that is capable of detecting a gaseous germicide. A filter layer is disposed between the barrier layer and the first end of the housing operable to filter flow through said housing.

An advantage of the present invention is a protective cap assembly for endoscopes that prevents decontamination chemistries from entering the interior portions of the endoscope during a decontamination process.

Another advantage of the present invention is a cap assembly as described above for use in low pressure decontamination systems.

A still further advantage of the present invention is a cap assembly as described above that compensates for pressure differentials between the exterior of an endoscope and the interior of an endoscope during a decontamination process.

A still further advantage of the present invention is a cap assembly as described above having a pressure relief valve to release pressure differentials that exist between the interior and exterior of the endoscope following a decontamination process.

A still further advantage of the present invention is a cap assembly as described above that finds advantageous application in a hydrogen peroxide low pressure decontamination process.

BRIEF DESCRIPTION OF THE DRAWINGS

FIG. 3 is an enlarged sectional view of a cap assembly, according to a second embodiment of the present invention, mounted to an equilibrium port of an endoscope (shown in phantom);

FIG. 6 is a sectional view of a second type of end connector for connecting the cap assembly to an endoscope, illustrating how the present invention may be modified to attach to different ports on different types of endoscopes.

DETAILED DESCRIPTION OF THE PREFERRED EMBODIMENTS

Figure 1:
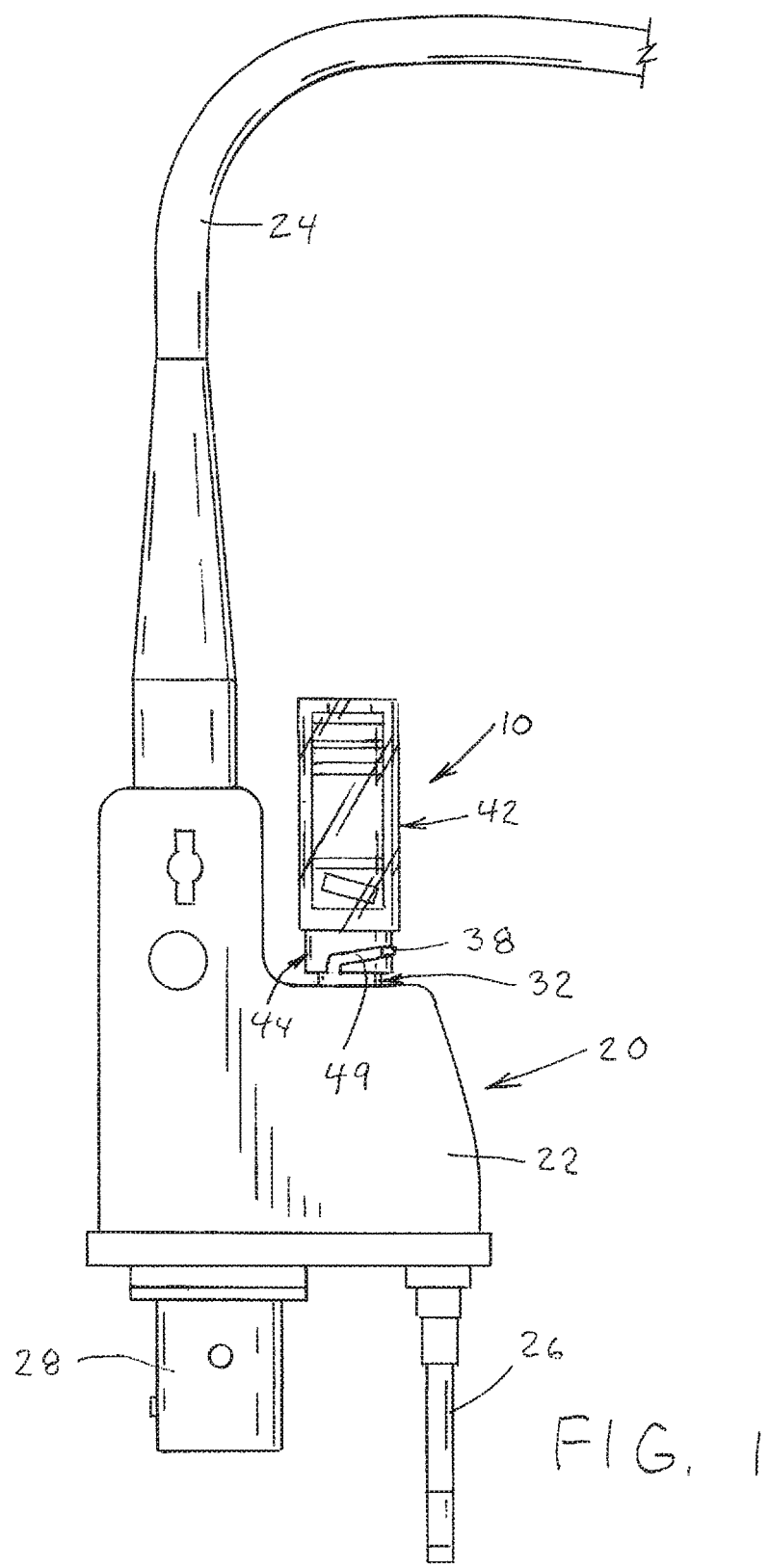
FIG. 1 is a partial view of a flexible endoscope showing a cap assembly, according to one embodiment of the present invention, covering an equilibrium port of an endoscope.
Figure 2:
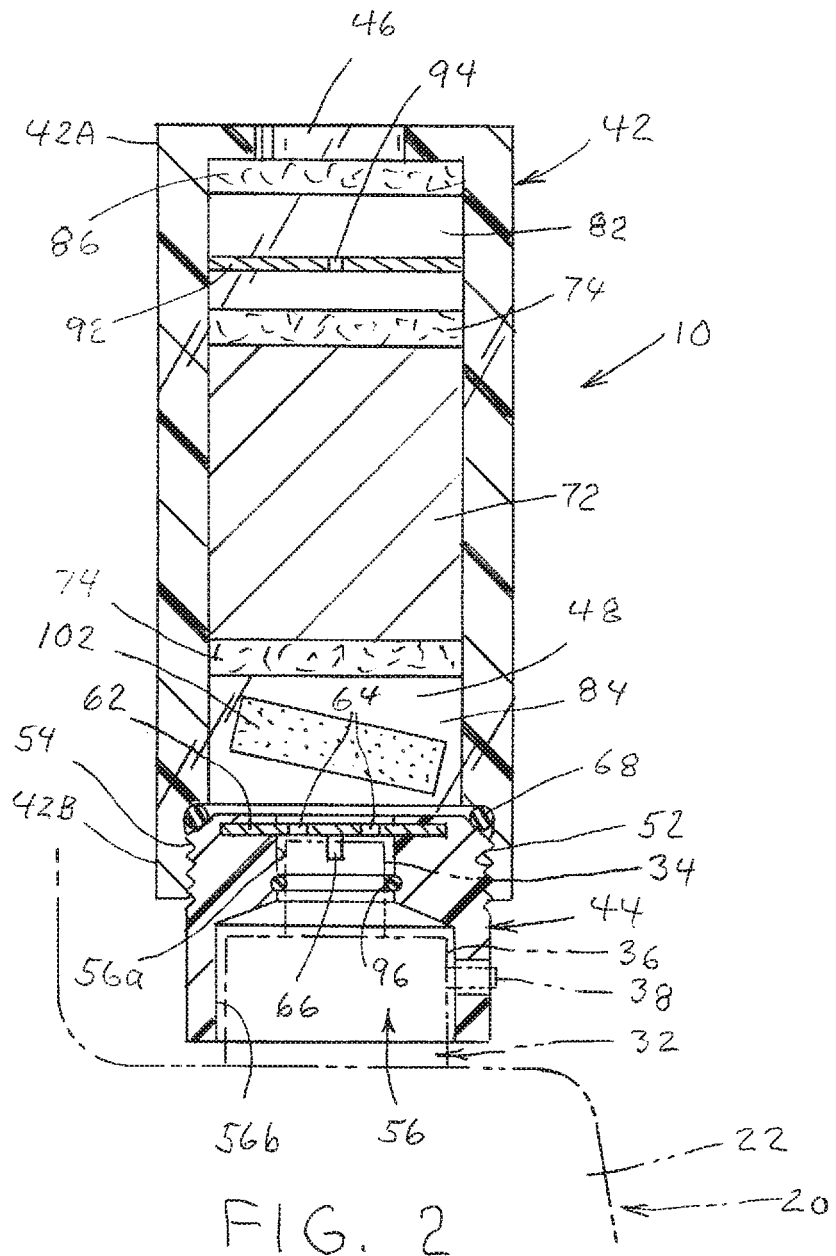
FIG. 2 is an enlarged sectional view of the cap assembly shown in FIG. 1.

Referring now to FIGS. 1 and 2, a cap assembly 10 for protecting the internal structures of an endoscope during a decontamination process is shown. FIGS. 1 and 2 show a cap assembly 10 illustrating a first embodiment of the present invention.

By way of background, FIG. 1 shows an endoscope 20 having a central body 22 and a flexible insertion tube 24 (partially shown) extending from body 22. Body 22 includes a flexible tube 26 operable to connect to and receive an optic device or an air source (not shown) and an electrical connection 28. Body 22 further includes an equalization port 32 that communicates with internal components with body 22 of the endoscope. In and of itself, endoscope 20 forms no part of the present invention, and has been described to better understand the use and purpose of the cap assembly 10 according to the present invention.

Cap assembly 10 is generally comprised of a tubular housing 42 having a mounting section 44, adapted to attach cap assembly 10 to equalization port 32 of endoscope 20. Housing 42 (best seen in FIG. 2) is generally tubular in shape and has a first end 42A with an aperture 46 therethrough and a second end 42B where the mounting section 44 is attached.

Housing 42 defines an inner chamber 48 that extends through housing 42. Aperture 46 in first end 42A of housing 42 communications with inner chamber 48. In the embodiment shown, internal screw threads 52 are formed along the inner surface of housing 42 at second end 42B thereof.

Mounting section 44 is generally cylindrical in shape and is dimensioned to be releasably mounted to second end 42B of housing 42. In the embodiment shown, mounting section 44 includes external threads 54 along a first end thereof. External threads 54 are dimensioned to matingly engage internal threads 52 along the inner surface of second end 42B of housing 42 to allow mounting section 44 to be threadably attached thereto, as shall be described in greater detail below. An internal passageway 56 extends axially through mounting section 44. Passageway 56 has a small diameter section 56a to receive a nozzle 34 on equalization port 32 of endoscope 20 and a large diameter section 56b. Large diameter section 56b is dimensioned to receive a base portion 36 of equalization port 32 of the endoscope 20. An actuating plate 62 is embedded in mounting section 44 and traverses small diameter section 56a of passageway 56. One or more apertures 64 are formed in plate 62. A pin 66 extends from plate 62 into equalization port 32. Pin 66 is dimensioned to engage a valve element (not shown) within the equalization port 32 of endoscope 20 and to move the valve element to allow airflow through equalization port 32, as is conventionally known.

As best seen in FIG. 2, mounting section 44 is dimensioned to be threadably received in second end 42B of housing 42. A seal element 68 is disposed between mounting section 44 and internal surfaces of housing 42 to form a seal therebetween. Together, the housing 42 and mounting section 44 define interior chamber 48 within cap assembly 10. Chamber 48 communicates with aperture 46 through first end 42A of housing 42 and with passageway 56 in mounting section 44 at second end 42B of housing 42.

A barrier layer 72 formed of a reactive material is disposed within chamber 48 of the housing 42. In the embodiment shown, barrier layer 72 is disposed generally centrally between first and second ends 42A, 42B of housing 42. Barrier layer 72 is formed of a material capable of absorbing or breaking down, i.e., destroying, a germicide used to decontaminate an endoscope. In this respect, in one embodiment of the present invention, the barrier layer 72 is formed of a material capable of breaking down (destroying) vaporized hydrogen peroxide. A filter layer 74 is disposed adjacent each side of barrier layer 72. Barrier layer 72 and adjacent filter layers 74 are dimensioned to define a first cavity 82 at first end 42A of housing 42 and a second cavity 84 at second end 42B of the housing 42. A third filter layer 86 is disposed within first cavity 82 adjacent aperture 46 at first end 42A of housing 42. Third filter 86 is dimensioned to prevent particles from entering into housing 42 through aperture 46.

Disposed within first cavity 82 is a plate 92 that basically traverses and separates first cavity 82 into two sections. An aperture 94 is formed within plate 92 to communicate one side of plate 92 to the other side of plate 92. Aperture 94 is a predetermined dimension as shall be described in greater detail below. Second chamber 84 is defined between the filter layer 74 adjacent destroyer layer 72 and mounting section 44. Second chamber 84 is dimensioned to receive an indicator test strip 102 that can provide an indication of exposure to a germicide, such as sterilized hydrogen peroxide.

Cap assembly 10 is adapted for mounting onto equalization port 32 of endoscope 20 as schematically illustrated in FIG. 2. In the embodiment shown, mounting section 44 includes a generally L-shaped slot 49 (best seen in FIG. 1) that extends from the free end of mounting section 44. A seal element 96 is provided between mounting section 44 and equalization port 32 to form a fluid-tight seal therebetween. A tab 38 (shown in phantom in FIG. 2) of equalization port 32 of endoscope 20 is used for attaching cap assembly 10 to endoscope 20 in a bayonet-like locking manner. Once cap assembly 10 is attached to endoscope 20, pin 66 on actuating plate 62 within mounting section 44 opens a valve (not shown) within equalization port 32 to allow flow therethrough.

Referencing now to the operation of the cap assembly 10, once mounted to an endoscope 20, endoscope 20 and cap assembly 10 can be inserted into a decontamination system, such as a vaporized hydrogen peroxide sterilizer. In this respect, endoscopes are typically decontaminated in low pressure systems wherein the pressure within the system changes between a vacuum and atmospheric pressure. The present invention allows for pressure changes within the system to communicate to the interior of endoscope 20 while preventing actual germicide, such as vaporized hydrogen peroxide, from entering endoscope 20. More specifically, aperture 46 in first end 42A of housing 42 allows germicide to be forced into housing 42 during situations where the pressure outside housing 42 and outside endoscope 20 may be higher than the pressure within endoscope 20. For example, during a low pressure sterilization cycle, a vacuum is typically established within the chamber of the system, which vacuum causes air within endoscope 20 to be drawn from within endoscope 20 through passageway 56 in mounting section 44, through internal chamber 48 of housing 42 and through aperture 46 at first end 42A of housing 42. In this respect, filter layers 74, 86 and destroyer or absorption layer 72 within cap assembly 10 are generally porous to allow pressure changes to be transmitted through housing 42. Aperture 94 in plate 92 and apertures 64 in actuating plate 62 are dimensioned to prevent rapid pressure changes to be experienced within the endoscope 20. Under low vacuum conditions where gaseous germicide may exist outside endoscope 20 and cap assembly 10, removing the vacuum and increasing the pressure in the internal chamber of the system can cause germicide within the system to be forced into housing 42 through aperture 46. Filter layer 86, disposed immediately within aperture 46 of housing 42 filters air flowing into housing 42 and prevents any debris within the chamber from being drawn into endoscope 20. Plate 92 with the single aperture 94 therethrough prevents a rapid pressure change within endoscope 20. According to one aspect of the present invention, germicide entering barrier layer 72 is absorbed or destroyed within barrier layer 72. When vaporized hydrogen peroxide is used, barrier layer 72 is preferably formed of absorbing or catalytic destroying materials, wherein the hydrogen peroxide would be absorbed or broken down to water and oxygen. Absorbing materials could consist of any material that will physically absorb hydrogen peroxide (or other germicide), such as foams, tubing, sheets or beads of materials such as polyurethane, silicone, polypropylene, and high density polyethylene (HDPE). Destroying materials could be any material that breaks down hydrogen peroxide (or other germicide)

such as oxidizable materials and heterogeneous (e.g., $MnO_2$, $PbO_2$), homogeneous (e.g., $FeO_3$, K1) or enzymatic (e.g., catalase) catalysts. The destroying materials can be supported on a material for use, e.g., polypropylene, HDPE substrate, Preferably, none of the hydrogen peroxide would flow pass barrier layer 72 into endoscope 20 during such changes in pressure within the chamber. Test indicator 102 within 42 housing can provide an indication, e.g., through color change, whether gaseous germicide has entered into second cavity 84 passed destroyer material 72. In this respect, housing 42 may be formed of a clear polymer material to allow visual inspection of test strip 102 within housing 42 following a decontamination cycle. Any indication, e.g., color change, can signify that cap assembly 10 is no longer effective in preventing germicide from entering endoscope 20. Thereafter, a new cap assembly 10 can be mounted to an endoscope prior to the next reprocessing cycle.

According to one aspect of the present invention, in mounting section 44, cap assembly 10 is adapted to mount to an equalization port 32 on endoscope 20. As will be appreciated by those skilled in the art, numerous types of endoscopes can have different types of equalization ports 32, with different configurations and sizes. In this respect, a particular mounting section can be designed to accommodate each type of equalization port 32 of endoscope 20. FIG. 6 shows how a different mounting section 44' can be attached to housing 42 to adapt to a different equalization port 32' on an endoscope.

FIG. 6 shows an equalization port 32' having a nozzle portion 34'. As seen in the drawings, nozzle portion 34' of equalization port 32' is smaller in diameter than the corresponding portion of equalization port 32 shown in FIGS. 2 and 3. A mounting section 44' is dimensioned to be received in second end 42B of housing 42 and have a lower end dimensioned to be mounted on equalization port 32' with a seal element 68 disposed between mounting section 44' and nozzle portion 34' of equalization port 32'. As illustrated in FIG. 6, an appropriate mounting section 44 can be designed and adapted to match the equalization port for a specific endoscope 20. As will be appreciated, the thread portion for all mounting sections would essentially be the same to allow attachment of a mounting section to housing 42. In another respect, the ability of housing 42 to be detached from mounting section 44 allows access to indicator strip 102 and replacement thereof when necessary. In the event that housing 42 is not clear, removal of the mounting section following each decontamination cycle can allow an operator of a system to visually inspect the indicator strip by removing mounting section 44 from housing 42.

The present invention thus provides a method of protecting the internal components of an endoscope from both harmful decontamination agents and the effect of large pressure differentials if the endoscope is reprocessed within a vacuum pressure system.

Figure 4:
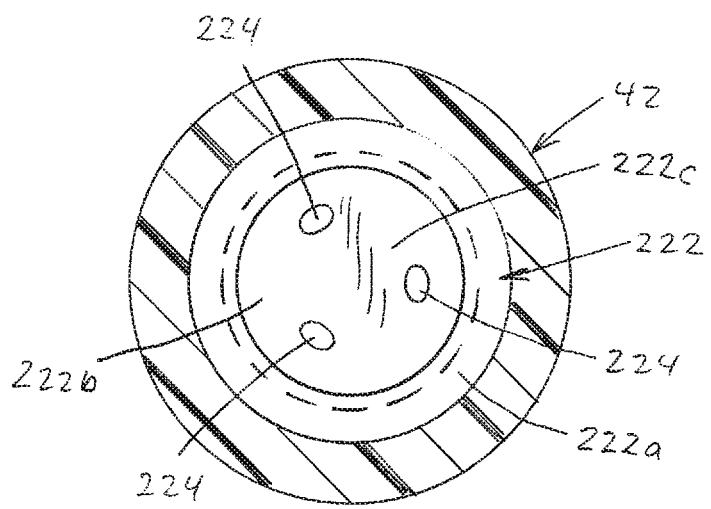
FIG. 4 is a sectional view taken along the lines 4-4 of FIG. 3.
Figure 5:
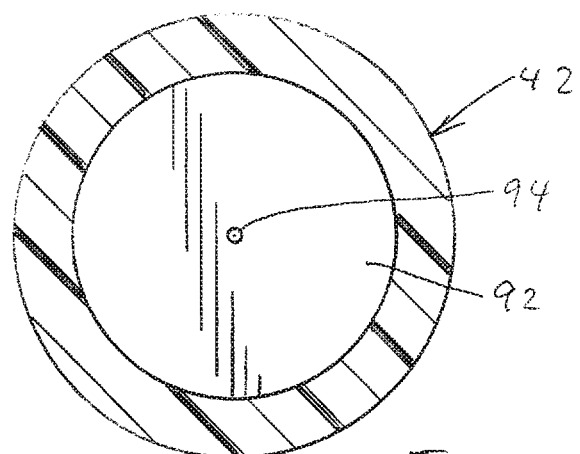
FIG. 5 is a sectional view taken along the lines 5-5 of FIG. 3.

Referring now to FIGS. 3, 4, and 5, a cap assembly 210 according to a second embodiment of the present invention is shown. Cap assembly 210 is essentially the same as cap assembly 10 with the exception that cap assembly 210 includes a flexible, resilient diaphragm 222 between plate 92 and filter layer 86 at first end 42A of housing 42. In addition, a relief valve 232 is provided in a port 234 that extends through housing 42 to chambers 48 below plate 92. As illustrated in FIGS. 3 and 4, resilient diaphragm 222 is generally cup-shaped and includes an annular flange 222a and a cup-shaped portion 222b having a flat end 222c dimensioned to engage the surface of plate 92. Spaced apart apertures 224 are formed within flat portion 222c of diaphragm 222. As best seen in FIG. 3, flat end 222c of diaphragm 222 is dimensioned to abut plate 92 with a solid central area of diaphragm 222 overlying aperture 94 in plate 92.

Pressure relief valve 232 communicates with chamber 48 in housing 42 on the opposite side of plate 92. Then diaphragm 222 communicates with a space defined between plate 92 and destroyer or absorption layer 72. Relief valve 232 is a directional valve that releases pressure within the upper compartment of housing 42 when a predetermined pressure has been exceeded. Moreover, diaphragm 222 is designed to be flexibly movable away from plate 92 when a certain pressure below plate 92 exceeds the pressure above plate 92 and above diaphragm 222. In this respect, during a decontamination process, establishing a vacuum in a chamber produces a vacuum outside of the housing. Because the pressure within endoscope 20 was originally at atmospheric pressure, a greater pressure exists within endoscope 20 than exists outside endoscope 20 and outside the cap assembly 210. The low pressure outside cap assembly 210 is experienced along the inner surface of diaphragm 222 which causes diaphragm 222 to move upward away from plate 92 when viewed from the orientation shown in FIG. 3. Eventually, openings 224 in diaphragm 222 and aperture 94 in plate 92 will equalize the pressure above and below diaphragm 222 and plate 92 and the resiliency of diaphragm 222 will again close flat end 222c of diaphragm 222 against plate 92 in a sealing fashion.

Having described the invention, the following is claimed:
1. A cap assembly for attachment to an equalization port on an endoscope, comprising:
   a tubular housing having a first end and a second end and defining an internal chamber extending from said first end to said second end;
   a mounting section releasably attached to said second end of said housing in fluid-tight fashion, said mounting section dimensioned to be attached to said equalization port of an endoscope in fluid-tight fashion, wherein said internal chamber communicates with said equalization port;
   a barrier layer formed of a reactive material that is capable of absorbing or breaking down a gaseous germicide, said barrier layer disposed within said internal chamber between said first end and said second end of said housing;
   a first cavity defined between said barrier layer and said first end of said housing;
   a second cavity defined between said barrier layer and said mounting section, said second cavity dimensioned to receive an indicator test strip that is capable of detecting said gaseous germicide;
   a filter layer disposed between said barrier layer and said first end of said housing operable to filter flow through said housing; and
   a plate disposed in and across said internal chamber between said filter layer and said barrier layer, said plate having an aperture therein, said aperture dimensioned to regulate flow though said plate and through said internal chamber, wherein the plate is configured to regulate a rate of pressure change from a first side of the plate to a second side of the plate, the second side opposite the first side, and
   wherein the housing includes a portion that enables visual inspection of the second cavity.

2. A cap assembly for attachment to an equalization port on an endoscope according to claim 1, wherein said mounting section is threadably attached to said housing.

3. A cap assembly for attachment to an equalization port on an endoscope according to claim 1, further comprising a second filter layer disposed between said barrier layer and said second cavity.

4. A cap assembly as defined in claim 1, further comprising another filter layer disposed between said plate and said barrier layer.

5. A cap assembly for attachment to an equalization port on an endoscope, comprising:
　a tubular housing having a first end and a second end and defining an internal chamber extending from said first end to said second end;
　a mounting section releasably attached to said second end of said housing in fluid-tight fashion, said mounting section dimensioned to be attached to said equalization port of an endoscope in fluid-tight fashion, wherein said internal chamber communicates with said equalization port;
　a barrier layer formed of a reactive material that is capable of absorbing or breaking down a gaseous germicide, said barrier layer disposed within said internal chamber between said first end and said second end of said housing;
　a first cavity defined between said barrier layer and said first end of said housing;
　a second cavity defined between said barrier layer and said mounting section, said second cavity dimensioned to receive an indicator test strip that is capable of detecting said gaseous germicide;
　a filter layer disposed between said barrier layer and said first end of said housing operable to filter flow through said housing;
　a plate disposed in and across said internal chamber between said filter layer and said barrier layer, said plate having an aperture therein, said aperture dimensioned to regulate flow though said plate and through said internal chamber; and
　a diaphragm disposed between said plate and said filter layer, said diaphragm having a flat surface dimensioned to engage and obstruct said aperture in said plate.

6. A cap assembly as defined in claim 5, wherein said diaphragm is cup-shaped wherein said flat surface defines the bottom of said cup-shape, said diaphragm having a normal position with said flat surface engaging said plate.

7. A cap assembly as defined in claim 6, wherein said diaphragm includes a plurality of apertures disposed in said flat surface thereof, wherein said diaphragm is movable away from said plate when pressure on one side of said diaphragm exceeds the pressure on another side of said diaphragm.

8. A cap assembly as defined in claim 6, further comprising a relief valve disposed between said third filter and said plate, said valve operable to relieve a vacuum in said first cavity on one side of said plate.

9. A cap assembly for attachment to an equalization port on an endoscope, comprising:
　a tubular housing having a first end and a second end and defining an internal chamber extending from said first end to said second end;
　a mounting section releasably attached to said second end of said housing in fluid-tight fashion, said mounting section dimensioned to be attached to said equalization port of an endoscope in fluid-tight fashion, wherein said internal chamber communicates with said equalization port;
　a barrier layer formed of a reactive material that is capable of absorbing or breaking down a gaseous germicide, said barrier layer disposed within said internal chamber between said first end and said second end of said housing;
　a first cavity defined between said barrier layer and said first end of said housing;
　a second cavity defined between said barrier layer and said mounting section, said second cavity dimensioned to receive an indicator test strip that is capable of detecting said gaseous germicide; and
　a filter layer disposed between said barrier layer and said first end of said housing operable to filter flow through said housing,
　wherein the housing includes a portion that enables visual inspection of the second cavity, and the indicator test strip is arranged within the second cavity.

10. A cap assembly for attachment to an equalization port on an endoscope according to claim 9, wherein said mounting section is threadably attached to said housing.

11. A cap assembly for attachment to an equalization port on an endoscope according to claim 9, further comprising a second filter layer disposed between said barrier layer and said second cavity.

12. A cap assembly as defined in claim 9, further comprising a plate disposed in and across said internal chamber between said filter layer and said barrier layer, said plate having an aperture therein, said aperture dimensioned to regulate flow though said plate and through said internal chamber.

13. A cap assembly as defined in claim 12, further comprising another filter layer disposed between said plate and said barrier layer.

14. A cap assembly as defined in claim 9, further comprising a diaphragm disposed between said plate and said filter layer, said diaphragm having a flat surface dimensioned to engage and obstruct said aperture in said plate.

15. A cap assembly as defined in claim 14, wherein said diaphragm is cup-shaped wherein said flat surface defines the bottom of said cup-shape, said diaphragm having a normal position with said flat surface engaging said plate.

16. A cap assembly as defined in claim 15, wherein said diaphragm includes a plurality of apertures disposed in said flat surface thereof, wherein said diaphragm is movable away from said plate when pressure on one side of said diaphragm exceeds the pressure on another side of said diaphragm.

17. A cap assembly as defined in claim 15, further comprising a relief valve disposed between said third filter and said plate, said valve operable to relieve a vacuum in said first cavity on one side of said plate.

* * * * *